United States Patent [19]
Hennig

[11] Patent Number: 5,926,021
[45] Date of Patent: Jul. 20, 1999

[54] METHOD OF MAGNETIC RESONANCE IMAGING FOR THE TIME-RESOLVED IMAGING OF PULSATILE VESSELS (PROJECTION ANGIOGRAPHY)

[76] Inventor: Jürgen Hennig, Johann-von-Weerth-Str. 12, D-79100 Freiburg, Germany

[21] Appl. No.: 08/893,508

[22] Filed: Jul. 11, 1997

[30] Foreign Application Priority Data

Jul. 18, 1996 [DE] Germany .......................... 196 28 951

[51] Int. Cl.[6] .................................... G01V 3/175
[52] U.S. Cl. ................. 324/306; 324/301; 324/316; 324/309; 324/307; 324/314; 324/300; 324/320; 324/319; 600/316; 600/473
[58] Field of Search ................... 324/316, 300, 324/314, 309, 307, 320, 301, 319; 600/316, 473

[56] References Cited

U.S. PATENT DOCUMENTS

| | | | |
|---|---|---|---|
| 5,277,182 | 1/1994 | Koizumi et al. ...... | 128/653.3 |
| 5,352,979 | 10/1994 | Conturo ............. | 324/307 |
| 5,422,576 | 6/1995 | Kao et al. ........... | 324/309 |
| 5,435,303 | 7/1995 | Bernatein et al. ..... | 128/653.3 |
| 5,479,925 | 1/1996 | Dumoulin ............ | 128/653.3 |
| 5,509,412 | 4/1996 | Bahn ................ | 128/653.2 |
| 5,517,117 | 5/1996 | Mueller ............. | 342/306 |
| 5,746,208 | 5/1998 | Prince .............. | 128/653.3 |

FOREIGN PATENT DOCUMENTS 9604567 2/1996 WIPO .

OTHER PUBLICATIONS

Magnetic Resonance in Medicine 13, pp. 77–89 (1990): A. Haase: Snapshot Flash MRI. Applications to T1, T2, and Chemical–Shift Imaging.

Radiology 1991; 181:641–643 . Robert R. Edelman et al.: "Coronary Arteries Breath–hold MR Angiography".

Magnetic Resonance in Medicine 33; 713–719 (1995): Yi Wang et al.: "Respiratory Motion of the Heart: Kinematics and the Implications for the Spatial Resolution in Coronary Imaging".

Magnetic Resonance in Medicine 17, 126–140 (1991): D.G. Nishimura et al. "Flow–Independent Magnetic Resonance Projection Angiography".

J.F. Debatin et al.: "Contrast Enhanced 3D MR–Angiography of the Pulmonary Arteries in under 20 Seconds", Proceedings 4th Meeting ISMRM, 1996, p.161.

*Primary Examiner*—Louis Arana
*Assistant Examiner*—Brij B. Shrivastav
*Attorney, Agent, or Firm*—Paul Vincent

[57] ABSTRACT

A magnetic resonance imaging method comprises exciting spins in an investigation volume via a radio frequency pulse and the signal produced thereby is subsequently read-out after appropriate spatial encoding following a short echo time te. Repetition of the sequence required for spatial encoding occurs in a time interval tr under appropriate variation of the spatially encoding gradient. The radio frequency pulse utilized for excitation has a short time duration and therefore a large excitation band width so that a projection image through a thick projection slice is produced under application of no slice selection gradient or with only a weak slice selection gradient. The time interval tr is sufficiently minimized that the image recording time required for recording of an image lies in the range of one EKG cycle or below. This process of recording a projection image is continuously repeated and a contrast medium bolus administered during the course of this sequential recording. The number of repetitions and therefore the length of the sequential recording is chosen in such a fashion that the dependence of the time changes of the signals from blood vessels can be observed. Selective imaging of the vessels located in an investigation volume and having contrast medium flowing therethrough is then effected through an analysis of the sequentially recorded data. In this fashion one can record projection angiograms in a measurement time of less than 1 s.

14 Claims, 7 Drawing Sheets

METHOD OF MAGNETIC RESONANCE IMAGING FOR THE TIME-RESOLVED IMAGING OF PULSATILE VESSELS (PROJECTION ANGIOGRAPHY)

This application claims Paris Convention priority of German patent application 196 28 951.3 the complete disclosure of which is hereby incorporated by reference.

BACKGROUND OF THE INVENTION

The invention concerns a method of magnetic resonance imaging with which the spins are excited in an investigation volume using radio frequency pulses and the signal produced thereby is subsequently read out following a short echo time te following appropriate spatial encoding, wherein repetition of the sequence for spatial encoding is carried out in a time interval tr with appropriate variation of the spatial encoding gradients.

A method of this type is known in the art from the publication of Haase, Magnetic Resonance in Medicine 13, pages 77–89 (1990).

This type of method facilitates magnetic resonance imaging of pulsatile moving blood-vessels e.g. coronary arteries. A problem related to the imaging of these objects is the fact that the allowable measuring time for the observation is extremely short and must be substantially below the time of an EKG cycle in order to avoid artifacts due to changes in the signal intensity in consequence of pulsatile flow as well as due to pulsatile motion of the vessel. The imaging of twisted or helical-shaped vessels such as the coronary arteries has additional complications using a slice-selective method since the vessel moves out of the observation slice in a manner which is very difficult to predict.

In conventional MR-angiography, imaging is attempted with the assistance of a multi-slice method, wherein a plurality of phase encoding steps are recorded per excitation step in an EKG cycle so that the entire recording process can be carried out within a time interval of up to 30 s in the absence of breathing. With the assistance of this technology it is possible to sectionwise image at least the thicker sections at the beginning of the coronary arteries when the orientation of the vessel section to be observed coincides with the selected slice. A method of this kind is known in the art due to Edelman RR, Radiology 181:641 (1991).

An alternative means for the avoidance of artifacts due to breathing motion is the so-called Navigator Echo Technique (Wang Y., Magnetic Resonance in Medicine 33:713 (1995)). In both procedures additional fat suppression pulses can be used to improve the signal of the vessels relative to the environment. Both utilize slice selective data collection and allow for imaging of the vessel in a sectionwise manner if required.

The problem of spatial recording of geometrically complicated vessels can in principal be solved with the assistance of three-dimensional data recording methods and subsequent reconstruction in accordance with the maximum intensity algorithm. Complex vessel dependencies can also be properly imaged using bolus injections of contrast media and very fast gradient echo methods leading to a very high signal for blood in vessels. A method of this kind is known in the art through the publication of Debatin, Proceedings 4th Meeting ISMRM, 1966, page 161. However, imaging requires an amount of time which is long compared to a heart cycle. The moving heart and the coronary vessels can therefore only be imaged in a defocussed manner using such a method or not at all.

Another possibility for imaging spatially complex vessels is given by the projection method. Such methods were formerly proposed for MR angiography and are e.g. known in the art from the publication of Nishimura so (Magnetic Resonance in Medicine 1991 January; 17(1):126–40). However, projection techniques have very large interference in comparison to the slice-selective method or in comparison to three-dimensional techniques from incomplete suppression of signals from stationary tissue due to the effective large thickness of the observed slice. Due to this fact techniques of this type are no longer used in MR angiography. Rather a desired view of a two-dimensional projection through a thick three-dimensional slice is effected by post-processing of three-dimensional recordings with the assistance of the so-called maximum intensity projection (MIP) algorithm.

It is therefore the purpose of the present invention to present a method for time-resolved MR angiography which is capable of recording projection angiograms in a measuring time of less than 1 s.

SUMMARY OF THE INVENTION

This purpose is achieved in accordance with the invention in that the radio frequency pulse utilized for excitation has a short time duration and therefore a large excitation band width so that a projection image through a thick projection slice is produced without a slice selection gradient or using only a weak slice selection gradient and the time interval tr is minimized to the extent that the time necessary for recording an image is in the range of or less than the time of an EKG cycle, and this recording of a projection image is repeated in continuous time intervals, wherein, during execution of this time sequence recording, a contrast medium bolus is administered and the number of repetitions and therefore the length of the time sequence recording is chosen in such a fashion that the time-dependent change of the signal from the blood-vessel can be observed and, finally, a selective imaging of the vessels through which contrast media are flowing and which are located in the investigation volume can be effected through analysis of the sequentially recorded data.

The method in accordance with the invention therefore partially combines features which are, to a certain extent known in the art, however, in a different context.

1. Utilization of a very fast $T_1$ weighted recording technique such as a gradient echo sequence (snapshot-FLASH) for image recording of a 256×256 image in less than 1 second. Carrying out the recording using large flip angles to maximize the $T_1$ contrast.
2. Carrying out the recording using the projection method either in its entirety without slice-selection or with selection of one thick slice encompassing the entire target volume.
3. Carrying out the recording using EKG triggering so that one image is produced per EKG trigger. The recording is then executed in such a fashion that, with very fast recording sequences, the entire image recording takes place in the diastolic phase of the heart cycle and therefore in a state of relative rest or, with somewhat faster recording sequence in the subsecond range, at least the low phase encoding projections which are particularly important for image construction according to the two-dimensional Fourier transformation method occur during this resting phase.
4. Carrying out the recording after application of a contrast medium bolus, which causes a shortening of the longitudinal relaxation time $T_1$ so that, during the flow of the contrast material through the vessel, same appears with significantly increased signal intensity compared to that previously obtained.

When observing vessel regions of the body which are moving due to breathing, the recordings are carried out in such a fashion that no breathing occurs during the relevant time periods of flow of the contrast medium bolus.

The features of the dependent claims improve the method in accordance with the invention in an advantageous fashion. Further advantages of the invention can be derived from the description and the drawing. The above mentioned features and those to be described further below can be utilized in accordance with the invention individually or collectively in arbitrary combination. The embodiments shown and described are not to be considered as exhaustive enumeration, rather have exemplary character only to illustrate the invention. The invention is represented in the drawing and will be more closely described with reference to the embodiments.

DESCRIPTION OF THE PREFERRED EMBODIMENT

The method in accordance with the invention is distinguished by a very high time resolution of less than 1 second for the recording of an MR angiogram, wherein the recording is carried out without slice selection to also facilitate recording of geometrically complex vessels. The recording is carried out using a very high $T_1$ weighted measuring sequence as contrast parameter to image the vessel and the time change in the vessel signal after application of a contrast medium material bolus. The recording is repeated during the relevant period of time of passage of the contrast medium bolus through the target vessel system. The vessel signal can then be separated from the background signal of stationary tissue using the time change of the observed signal intensity. The recording is carried out without breathing to avoid breathing artifacts.

Figure 1:
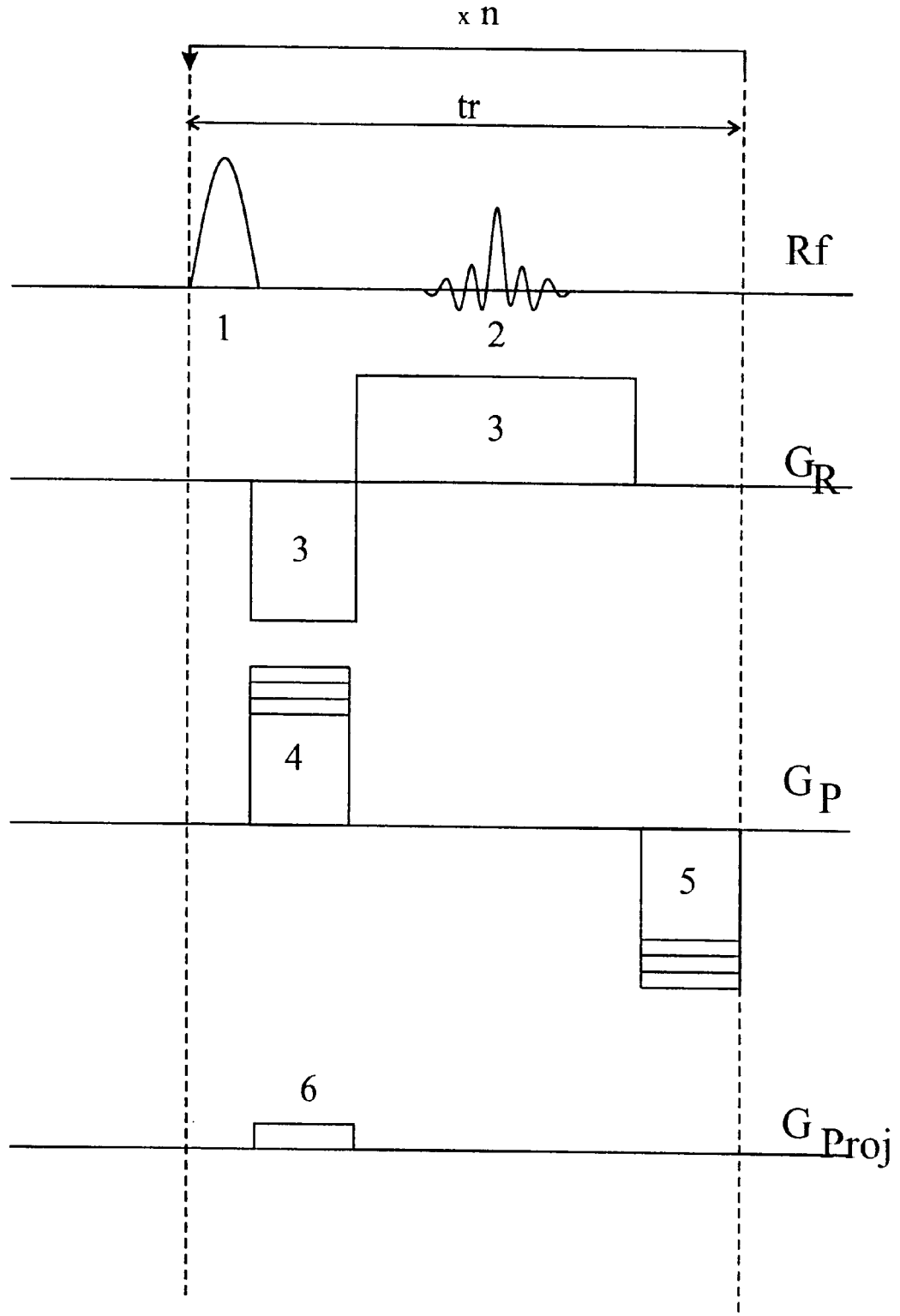
FIG. 1 shows a schematic time dependence of a measurement sequence in accordance with the invention having radio frequency excitation (Rf), switching of read-out gradients ($G_R$), phase encoding gradients ($G_P$) and projection gradients ($G_{proj}$)

A fast gradient echo sequence is utilized as measuring sequence with as small an echo time as possible to avoid so-called susceptibility as well as flow artifacts and using high excitation pulse flip angles to achieve as good a $T_1$ contrast as possible as well as a good suppression of the signal from stationary tissue. The time dependence of such a sequence is illustrated in FIG. 1. Rf indicates the radio frequency excitation pulse 1 as well as the signal 2 produced thereby, $G_R$ the read gradient 3, which causes signal read-out after an echo time te, $G_P$ the phase encoding gradient 4 and $G_{proj}$ the gradient 6 in the projection direction perpendicular to $G_R$ and $G_P$. "tr" is the repetition time for recording a phase encoding step.

The additional gradient 5 is optional. It serves to avoid artifacts during refocussing of the transverse magnetization over a plurality of repetition intervals. When eliminating the gradient 5 to achieve a shorter repetition time tr, the radio frequency pulses are preferentially applied with alternating phase to displace the resulting image artifacts by half an image width in the phase encoding direction.

The (small) gradient 6 in the projection direction is also optional. This serves for additional suppression of the signal from spatially extended structures in the projection direction compared to the signal from thin vessels.

Figure 2:
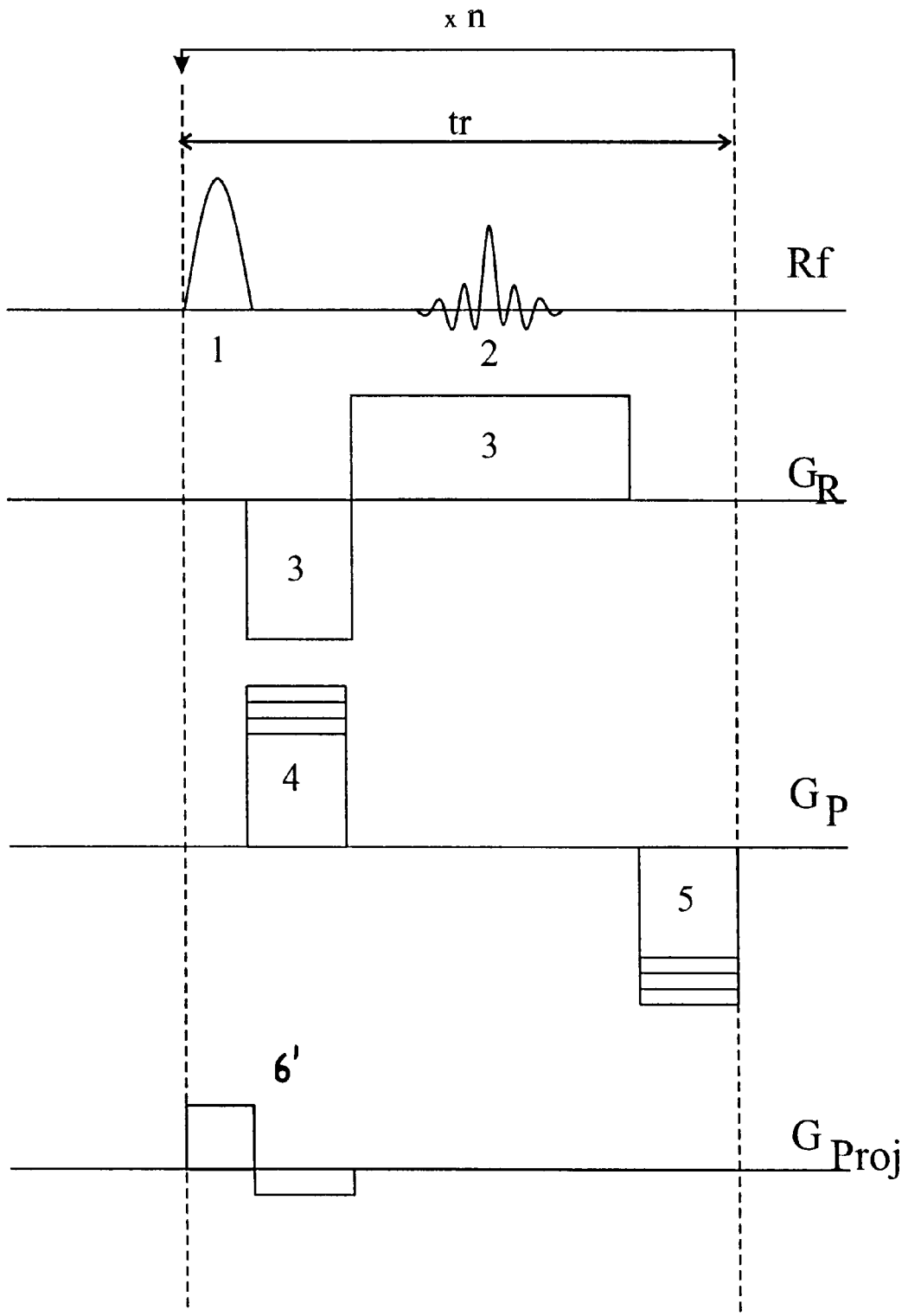
FIG. 2 shows a sequence as in FIG. 1 however with a small slice selection gradient in the projection direction.

FIG. 2 shows the sequence with the addition of a (small) slice selective gradient 6' in the projection direction to limit the projection volume. The sequence is repeated n times for image taking within the repetition interval tr under variation of the phase encoding gradient 4 (and if appropriate 5) until all data necessary for image reconstruction are recorded.

Figure 3:
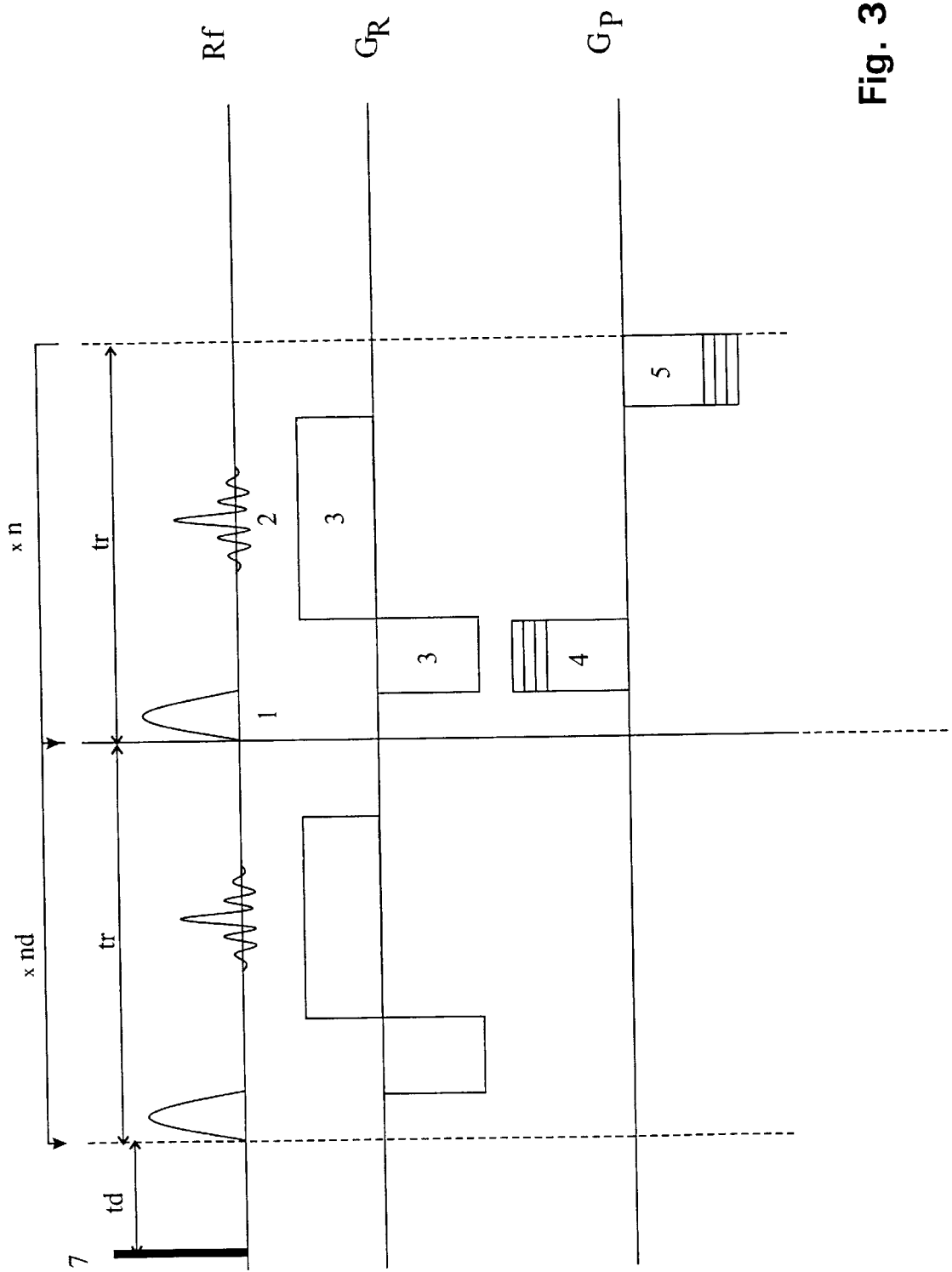
FIG. 3 shows a measurement sequence in accordance with the invention having EKG trigger pulses.

In FIG. 3, the entire image recording is started by a trigger pulse 7 derived from the EKG signal for the preferred application of observation of pulsatile flow. Nd so-called dummy projections are introduced prior to the actual image taking to bring the signal into a steady state. No signals are acquired during these nd dummy projections. In addition, a time td is introduced between the trigger pulse and the beginning of the sequence. The delay time td+nd×tr is adjusted through appropriate choice of td and nd such that the actual image recording takes place in the desired observation phase (preferentially diastolic and also in relative quiescence) within the EKG cycle.

The sequence can be extended through so-called fat suppression pulses for additional suppression of the signal from stationary tissue, since the signal from fat constitutes the largest fraction of the background signal due to its very short relaxation time $T_1$. In addition or alternatively, so-called magnetization transfer pulses can be introduced for additional suppression of stationary signals. Undesirable steady-state signal formation can be effected using so-called gradient spoiling and/or Rf spoiling. All these features are known in the art through the literature and can be integrated into the sequence by one of average skill in the art.

The method characterized in this fashion has very low intrinsic contrast for blood. The signals coming from vessels are only made visible by a strong shortening of the relaxation time $T_1$ using appropriate contrast medium.

The entire image recording is therefore continuously repeated m-times with or after application of a contrast medium bolus so that the time dependence of the signals prior to, during and after passage of the contrast medium bolus can be observed. The signal dependence in the vessels is then qualitatively distinguished by less signal until the begin of bolus flow, an increase in signal intensity within several seconds in dependence on the target volume up to the maximum value, and a subsequent signal decay to nearly the initial value following even distribution of the contrast medium in the blood stream and in contrast medium absorbing tissue. Typical times for the passage of the contrast medium are 5 to 20 seconds. The recordings are carried out without breathing during the substantial time of bolus transport to observe vessels in organs which move as result of breathing.

The measurement sequence is carried out with a choice of recording parameters (as short a tr and te as possible, larger flip angles (90°) for the excitation pulse and, if appropriate, additional measures described above for the suppression of stationary tissue signals) as well as with application of the contrast medium essential for signal production (bolus injection as quickly and with as defined an injection time as possible, preferentially mechanically by means of an injection pump and if appropriate increasing the contrast medium dosage and/or the contrast medium concentration) in such a fashion that the signal from blood in the vessels at the point of time of bolus transport compared to the signal of stationary tissue is optimized to the greatest extent possible.

The achievable times tr and te are thereby dependent on the power capabilities of the gradient system used. For systems with 25 mT/m gradient amplitudes and switching times of 0,3 ms, values of te=1.5–2 ms and tr=3–5 ms can easily be achieved. A shortening of te in comparison to conventional recording techniques with which the time window for data acquisition is chosen in such a fashion that the observed echo appears in the middle thereof, can be achieved through displacement of the echo into the first half of the acquisition window (so-called partial echo method).

The choice of the flip angle thereby depends on the power capability of the radio frequency transmitter as well as on the load capabilities of the transmitter coil utilized. The radio frequency pulses utilized in the projection method to reduce te are preferentially effected in the form of short (0.1–0.5 ms) pulses requiring high transmitter power to effect a 90° pulse. For reasons of patient protection, this can lead to the inability of achieving a flip angle of 90° (or even more) desirable for signal dependence.

The fraction of blood to be observed is very small compared to the fraction of stationary tissue along the projection direction. For this reason, even in the event of optimal choice of recording conditions, signals of stationary tissue are typically observed as possibly interfering background signals in the projection images. An improvement in image contrast with further reduction of the background signals can be achieved by taking advantage of the fact that the signal from vessels has a typical characteristic dependence caused by passage of the bolus, whereas the signal from stationary tissue remains constant or has a dependence determined by physiological processes (peristaltic, involuntary motion and so on).

The analysis of the m sequentially recorded projection images can be utilized in appropriate post-processing to distinguish the vessel signals from the background. A simpler and preferred algorithm therefor is correlation analysis. Towards this end, the m observed signals in each pixel are compared to a reference signal describing the dependence of the intensity during the bolus. The reference signal can be defined as an external signal through conventional bolus dependence or can be extracted from the measured data through the signal dependence of a pixel (or in a region of interest) in an image region recognized as a vessel.

The mathematical procedure of correlation analysis is known in the art from the literature and need not be repeated here.

A pixel by pixel representation of the correlation coefficients extracted in this fashion thereby yields an improved angiogram. By variation of the reference signal it is thereby possible to not only separate vessel signals from stationary tissue signals but also signals from vessels having flowing bolus from those first penetrated by the contrast medium at a later point of time. In this fashion, in addition to the anatomical representation of the vessels, information can be extracted from the data which is of possible diagnostic importance. Even diffuse signal changes due to the passage of the contrast medium through the capillary bed of the organ can be recognized in this manner to facilitate measurements of organ perfusion in addition to MR angiography.

A modification of the recording technique comprises changing the dependence of the time sequence recording to record a plurality of projection images under differing projection directions. This can be done in the simplest and preferred case as a bi-planar recording with which projection images are recorded at two differing angles. By combining two such recordings (if appropriate even as pseudo-three-dimensional representations by means of appropriate stereoscopic representation procedures), the observer can thereby gain information concerning the position of the vessel in the projection direction.

The acquisition of data for the differing projection directions can thereby either take place by means of sequential recordings of an entire projection image or in the otherwise conventional method of nested recording used in magnetic resonance imaging multi-slice methods with which each individual phase encoding step is initially recorded in all projection directions.

The measurement sequence described up to this point represents a preferred implementation given the current technical conditions in magnetic resonance imaging and yields good results for the principal application area of interest (imaging of pulsatile vessels, in particular the coronary arteries). In addition to the described procedure for carrying out the sequence as a gradient echo sequence with spatial encoding by means of phase gradients for image reconstruction in accordance with the method of two-dimensional Fourier transformation, the sequence can also be carried out using the procedure of spatial encoding according to the projection reconstruction method.

Figure 4:
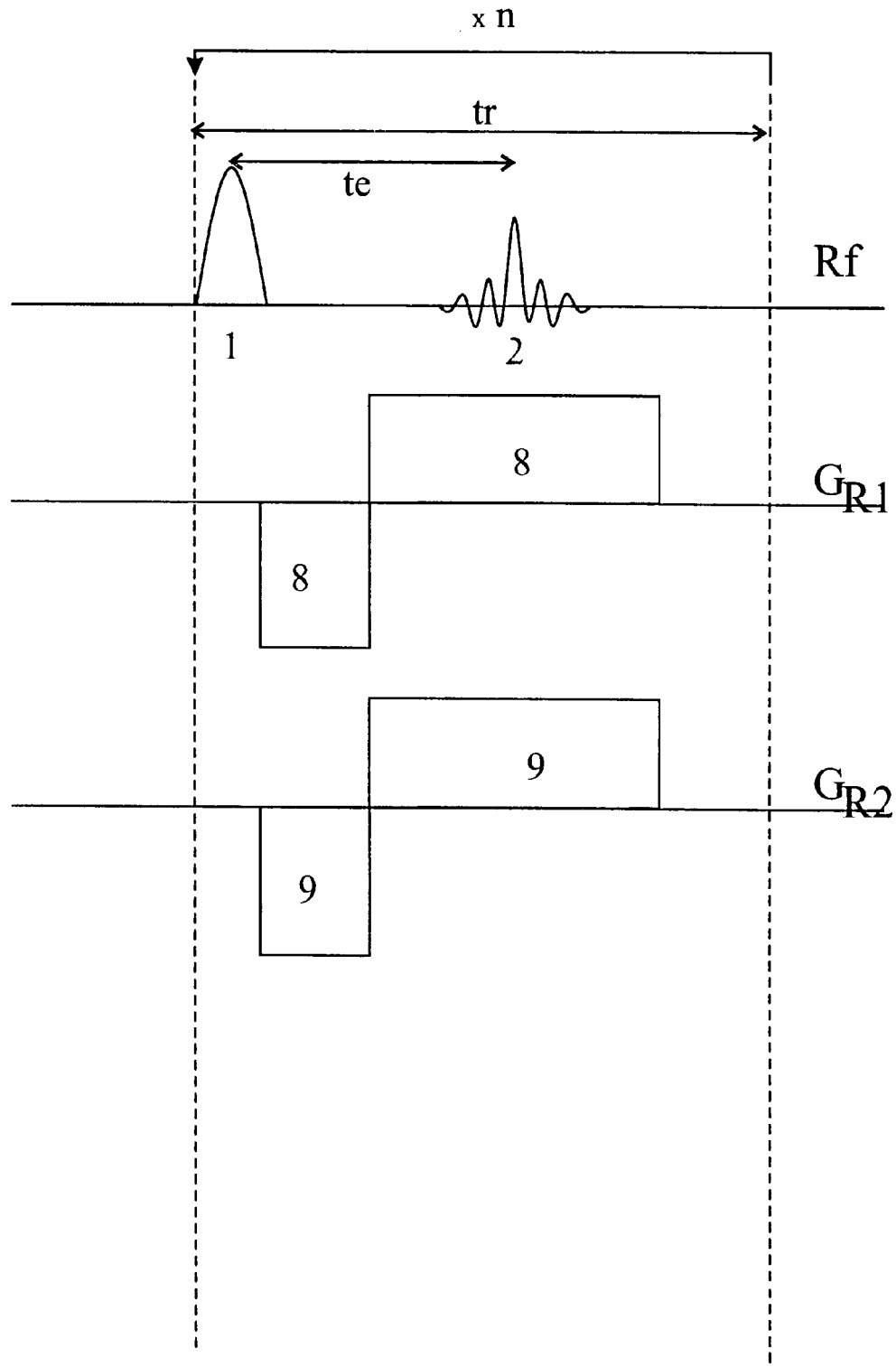
FIG. 4 shows a time diagram of a sequence in accordance with the invention having spatial encoding in accordance with the projection reconstruction method.

The corresponding modified basic sequence is shown in FIG. 4. The amplitude of the two gradients $G_{R1}$ and $G_{R2}$ designated with the reference symbols 8 and 9 respectively is thereby varied from recording step to recording step in such a fashion that signal read-out is effected at differing angles and with constant angle incrementation within the plane defined by the direction of the orthogonal gradients $G_{R1}$ and $G_{R2}$ and an image is calculated from this data set using the projection reconstruction method.

For special applications, additional modifications of the measurement sequence can be used. One such application is given in the event that the vessel dependence is to be observed in vessel sections which are near to the site of the bolus injection.

This is the case when injecting the contrast material in the conventional manner into the vein of the arm prior to all investigations of veins leading to the heart, but also for all applications with which the injection is done with a catheter introduced in the vicinity of the vessel to be investigated. In this case there is a very high concentration of contrast medium in the vicinity of the injection site which is then rapidly thinned during subsequent development. The high local contrast medium concentration then leads to a reduction in the signal due to an unavoidable property of all conventional contrast materials, namely the causing of susceptibility effects. Even with a normal dosage of contrast material of 0.1 mmol/kg of body weight, this can lead to a signal decay constant $T_2^*$ in the range of less than 1 ms. The signal then disappears in a gradient echo method even when utilizing a minimized echo time te in the range of 1.5–2 ms. Although this signal quenching can be avoided by lower dosage of the contrast medium, this leads, however, to the inability or extreme difficulty of imaging vessel sections which are far removed and in which a thinning of the contrast material has already taken place due to mixing with blood.

Figure 5:
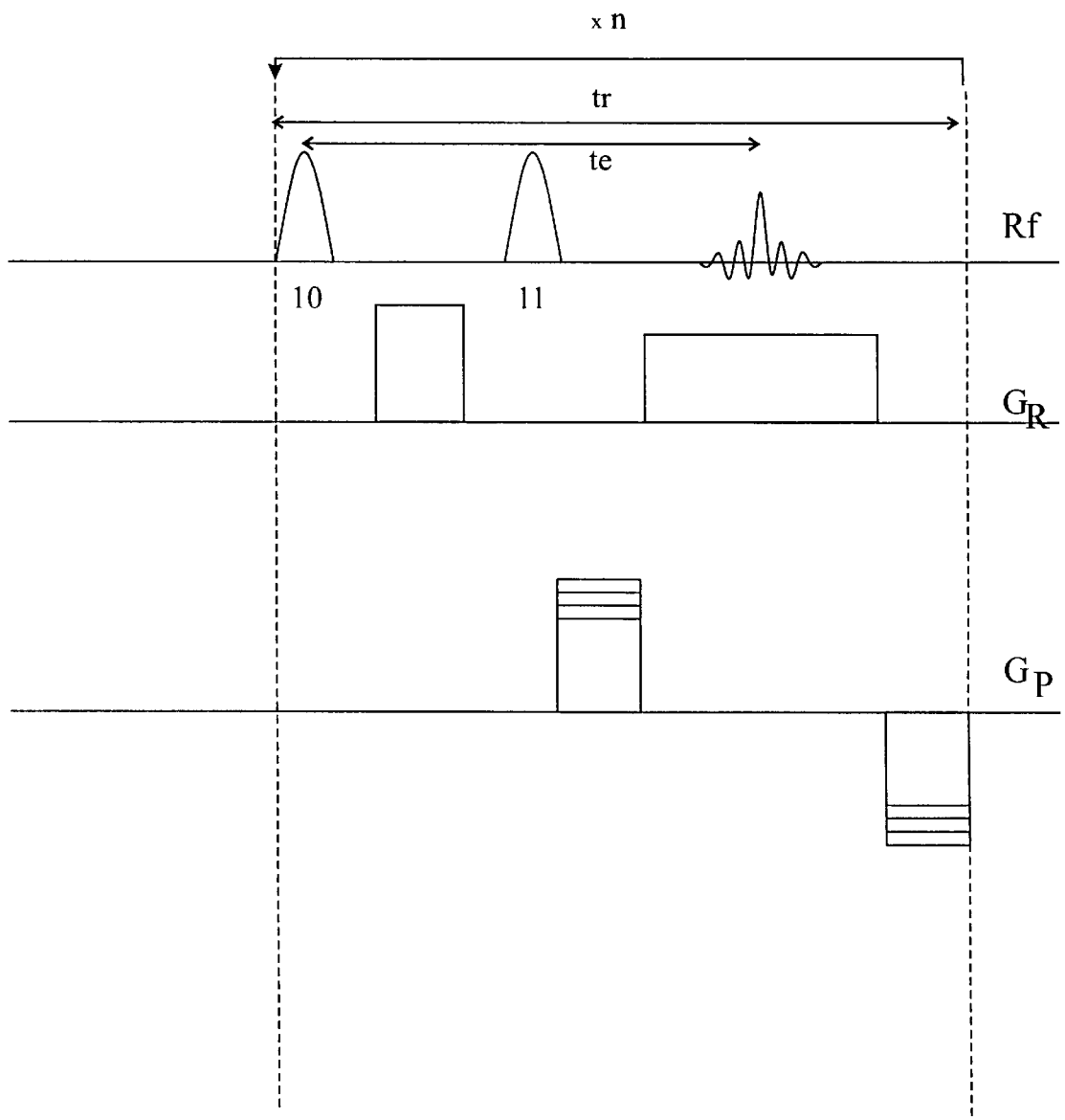
FIG. 5 shows a time diagram of a sequence in accordance with the invention using spin echoes instead of a gradient echo read-out.

A possibility for avoiding this signal loss is the application of a spin echo sequence instead of the gradient echo sequence. A basic sequence therefor is shown in FIG. 5. A sequence of two pulses comprising an excitation pulse 10 and a refocussing pulse 11 is utilized instead of the excitation pulse 1. With constant gradient power and otherwise constant processing, the minimum signal read-out time te (and thereby the repetition time tr) is lengthening compared to the gradient echo method shown in FIG. 1 by at least the duration of the additional refocussing pulse 11.

This modification has the additional disadvantage that the refocussing pulse 11 should, to achieve an optimum signal intensity, have a flip angle of 180° which is not always possible for technical reasons and for reasons of patient protection so that signal loss must be accepted for smaller flip angles.

An additional disadvantage of the sequence carried out in this fashion is the fact that, due to the differing saturation dependence of spin echo sequences compared to gradient echo sequences, the signal-to-noise ratio is significantly (approximately 2-fold) reduced compared to the preferred embodiment.

These disadvantages can, however, be compensated for using the above mentioned strong concentration gradient for the contrast medium in the region of interest and by avoiding signal loss due to susceptibility with the assistance of spin echo formation, so that only a small amount of signal decay occurs due to the relatively small reduction in the relaxation constant $T_2$.

Figure 6:
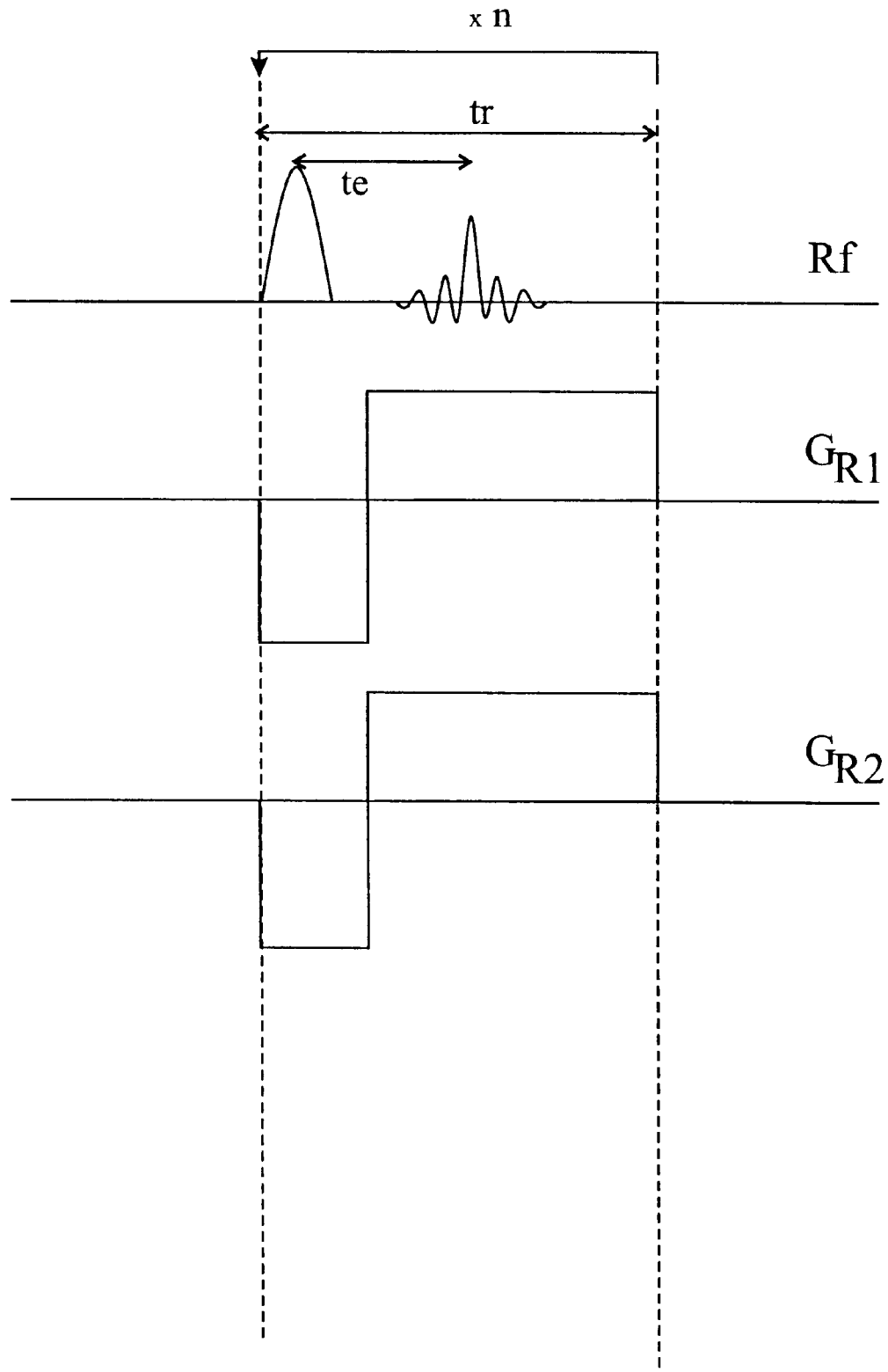
FIG. 6 shows a time diagram of a sequence in accordance with the invention utilizing a defocussing pulse for the production of a gradient echo during application of the excitation pulse.

Another modification which facilitates a reduction in the echo time te as well as in the repetition time tr compared to the method shown in FIG. 1, is shown in FIG. 6. The defocussing pulse necessary for production of a gradient echo already occurs during application of the excitation pulse. In addition to a reduction in te and tr, this procedure leads to a limitation of the observation volume within the image window should the band width of the excitation pulse be smaller than the recording band width used for data acquisition.

This can be a desirable effect for avoiding image artifacts. This embodiment is preferred, as shown in FIG. 6, in combination with a projection reconstruction method. It can, however, also be effected using image reconstruction in accordance with the Fourier transformation method, wherein the phase gradient required therefor can also be switched-on during the radio frequency pulse or directly thereafter. In this fashion a limitation in the observation window within the image plane is also hereby effected if the pulse band width is smaller than the recording band width. In addition, the change in the excitation profile effected by the phase gradients from one recording step to the next causes a successive defocussing of the image towards the edge of the selected volume within the image plane.

Figure 7:
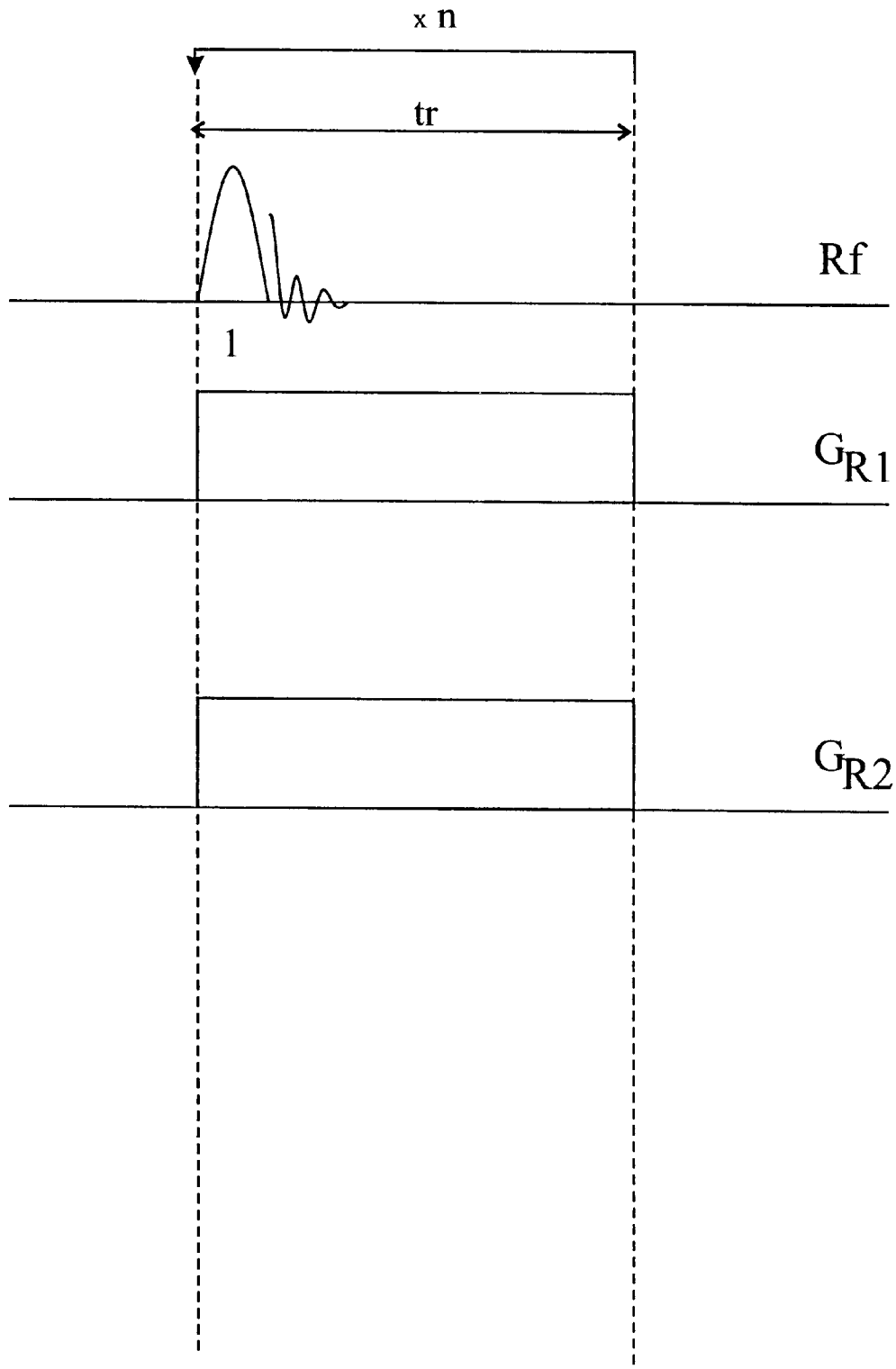
FIG. 7 shows a time diagram of a sequence in accordance with the invention having an FID signal directly after the end of the radio frequency pulse.

Finally, the most radical step for the reduction of tr and te can be effected by recording with gradients which no longer vary within a repetition interval tr, rather only from one recording step to the next in the manner of a spatial encoding. The basic sequence therefor is shown in FIG. 7. The signal here is present as a so-called free induction decay (FID) directly following the end of the radio frequency pulse. Spatial encoding in the form of projection reconstruction methods is also preferred here.

Due to the transformation properties of an FID compared to an echo, additional steps must, however, be taken in this case in order to avoid formation of image artifacts from signal distortions. This can be done through extension of the FID to an echo using symmetry properties, analogous to the so-called half-Fourier method. Alternatively, phase-sensitive reconstruction can be carried out with appropriate phase correction so that the real part of the complex image is focussed, whereas the dispersion portion of the complex transformed signal causing the defocussing remains in the imaginary portion.

Further modifications such as carrying out the experimental studies, if appropriate, with multiply repeated application of the contrast medium bolus and the possibilities for further signal analysis resulting therefrom are immediately obvious to one of average skill in the art after reading the above description of the invention and do not require further explanation here. The above mentioned means for additional suppression of the signal of stationary tissue (fat suppression, magnetization transfer, RF- and gradient spoiling) can be integrated by one of average skill in the art into the above described sequence.

I claim:

1. Method of magnetic resonance image comprising the steps of:
    a) irradiating a radio frequency pulse having a short time duration and a high band width to excite spins in a thick slice within an investigation volume;
    b) applying a spatial encoding gradient;
    c) recording a signal;
    d) repeating steps a) through c) to acquire data for constructing an image within a time interval tr, less than or equal to an EKG cycle time;
    e) continuously repeating step d) a plurality of times to acquire data for constructing a plurality of images over time;
    f) applying a contrast medium bolus during step e), wherein steps e) and f) for observing time changes in signal from blood vessels; and
    g) analyzing data recorded in steps a) through f) to selectively image blood vessels in said investigation volume which have said contrast medium bolus flowing therein.

2. The method of claim 1, wherein repetition of step b) comprises applying a projection gradient at differing projection angles.

3. The method of claim 1, wherein repetition of step b) comprises applying a phase encoding gradient for nested recording of phase encoding steps according to conventional magnetic resonance imaging multi-slice recording.

4. The method of claim 1, wherein steps a) through c) comprise a gradient echo sequence.

5. The method of claim 1, further comprising applying an additional gradient between step c) and repeated step a) to effect a dephasing caused by the action of spatial encoding gradients in an image plane which is constant with the respect to all gradients prior to each subsequent excitation pulse in step a).

6. The method of claim 1, further comprising applying an additional gradient between step c) and repeated step a) for dephasing a steady state signal of previously excited transverse magnetization.

7. The method of claim 1, wherein a reference phase is incremented in repeated steps a) and c) to destroy steady state signals according to the method of 'RF spoiling'.

8. The method of claim 1, wherein step a) comprises the step of alternating a phase of said radio frequency pulse between repetitions of step a) to displace image artifacts of transverse magnetization signals from previous recording steps by one half image width in a phase encoding direction.

9. The method of claim 2, wherein step g) comprises a projection reconstruction method.

10. The method of claim 1, wherein a reduction in an echo read-out time is effected by applying a spatial encoding gradient having critical timing prior to and during step a) to reduce an observation region in an image window in dependence on a ratio between said radio frequency pulse band width and a recording band width.

11. The method of claim 1, wherein spatial encoding gradients are not changed between step a) and c) to produce a free induction decay signal directly following said radio frequency pulse.

12. The method of claim 1, wherein steps a) through c) produce a spin echo sequence through sequential application of a refocussing pulse following step a).

13. The method of claim 1, further comprising applying an EKG derived trigger signal prior to step a).

14. The method of claim 13, further comprising multiple repetition of so-called dummy recording steps between said trigger signal and step a) to effect a steady state of a signal to be observed at the beginning of actual signal recording.

* * * * *